(12) United States Patent
Cline

(10) Patent No.: US 10,569,058 B2
(45) Date of Patent: Feb. 25, 2020

(54) INTRODUCER SHEATHS

(71) Applicant: EP Dynamics, Inc., Los Angeles, CA (US)

(72) Inventor: Sean Cline, West Lafayette, IN (US)

(73) Assignee: EP Dynamics, Inc., Los Angeles, CA (US)

( * ) Notice: Subject to any disclaimer, the term of this patent is extended or adjusted under 35 U.S.C. 154(b) by 0 days.

(21) Appl. No.: 15/594,400

(22) Filed: May 12, 2017

(65) Prior Publication Data
US 2018/0326185 A1 Nov. 15, 2018

(51) Int. Cl.
*A61M 25/00* (2006.01)
*A61M 25/06* (2006.01)
*A61M 39/06* (2006.01)
*A61B 17/34* (2006.01)

(52) U.S. Cl.
CPC ..... *A61M 25/0668* (2013.01); *A61B 17/3423* (2013.01); *A61M 25/0041* (2013.01); *A61M 25/0097* (2013.01); *A61M 39/06* (2013.01)

(58) Field of Classification Search
CPC .......... A61M 25/0105; A61M 25/0133; A61M 25/0136; A61M 25/0147; A61M 2025/01
See application file for complete search history.

(56) References Cited

U.S. PATENT DOCUMENTS

| | | | |
|---|---|---|---|
| 4,445,893 A | 5/1984 | Bodicky | |
| 4,682,981 A | 7/1987 | Suzuki et al. | |
| 5,242,441 A * | 9/1993 | Avitall | A61B 18/1492 600/374 |
| 5,968,008 A * | 10/1999 | Grams | A61M 1/0084 604/264 |
| 6,245,045 B1 * | 6/2001 | Stratienko | A61M 25/0041 604/164.13 |
| 7,398,125 B2 | 7/2008 | Osypka et al. | |
| 8,262,671 B2 | 9/2012 | Osypka | |
| 9,078,981 B2 | 7/2015 | Subramaniam et al. | |
| 9,554,817 B2 | 1/2017 | Goldfarb et al. | |
| 2008/0051707 A1 | 2/2008 | Phan et al. | |
| 2010/0249773 A1 * | 9/2010 | Clark | A61B 18/08 606/41 |
| 2011/0092910 A1 | 4/2011 | Schultz | |
| 2012/0109060 A1 | 5/2012 | Kick et al. | |
| 2014/0309661 A1 | 10/2014 | Sheps et al. | |

OTHER PUBLICATIONS

PCT application PCT/US2018/031692 (EP Dynamics 001 PCT), Jul. 27, 2018 ISR/WO.

* cited by examiner

Primary Examiner — William R Carpenter
(74) Attorney, Agent, or Firm — Jinn Su

(57) ABSTRACT

Introducer sheaths are described. In one embodiment, an introducer sheath comprises a sheath hub, a fixed housing coupled to the sheath hub, a rotating element rotatably coupled to the fixed housing, a sheath tube fixedly coupled to the rotating element, and a lock coupled to the rotating element. The lock is capable of preventing the rotating element and the sheath tube from rotating with respect to the sheath hub.

20 Claims, 11 Drawing Sheets

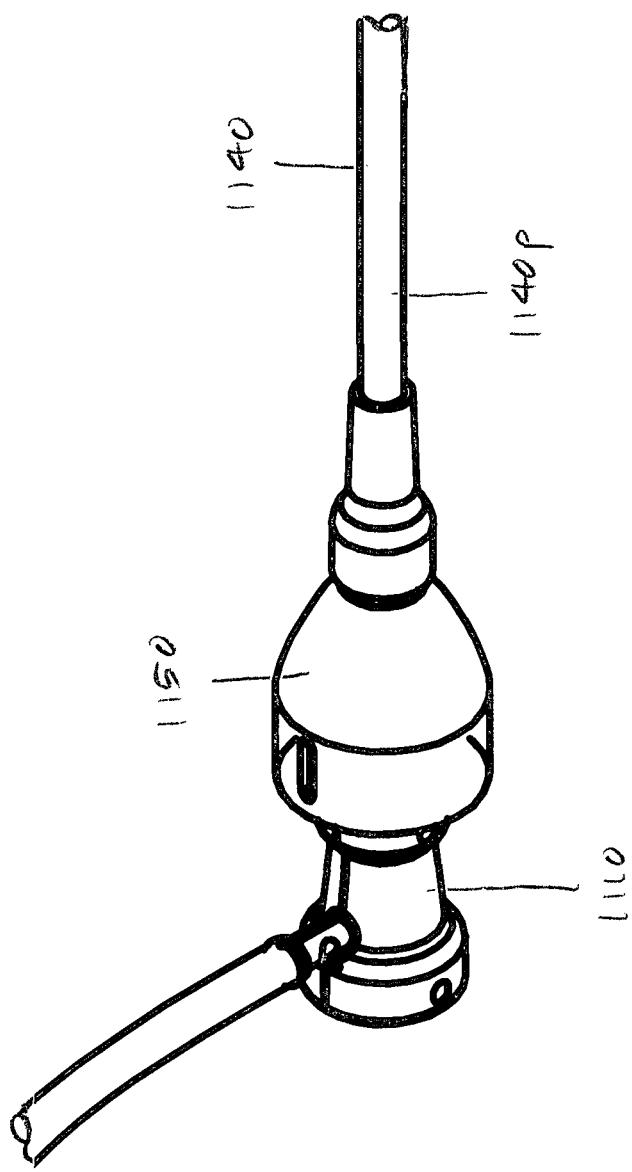

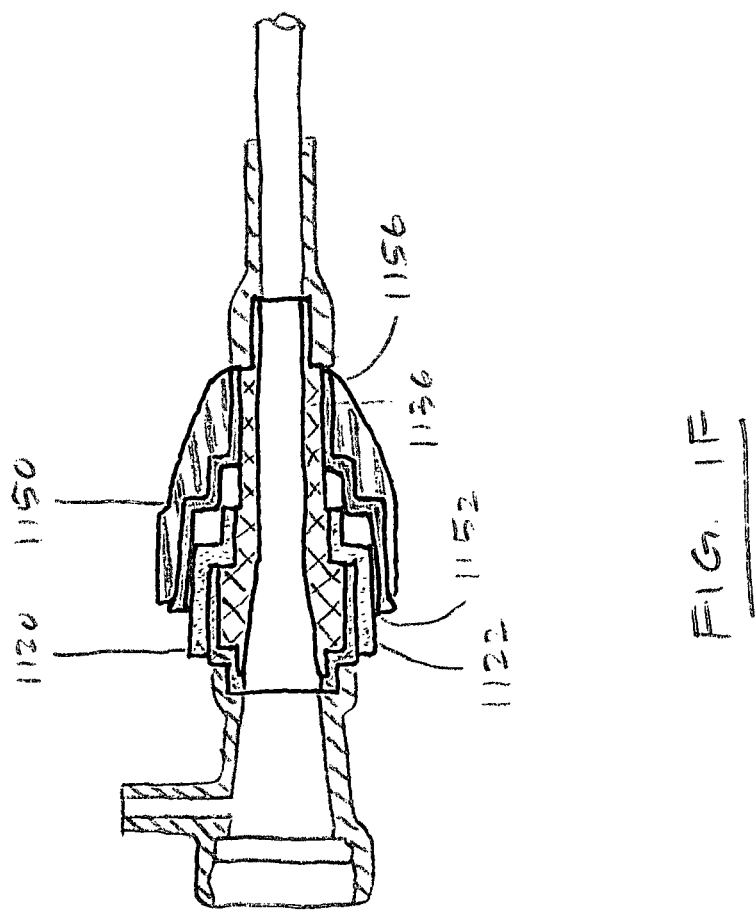

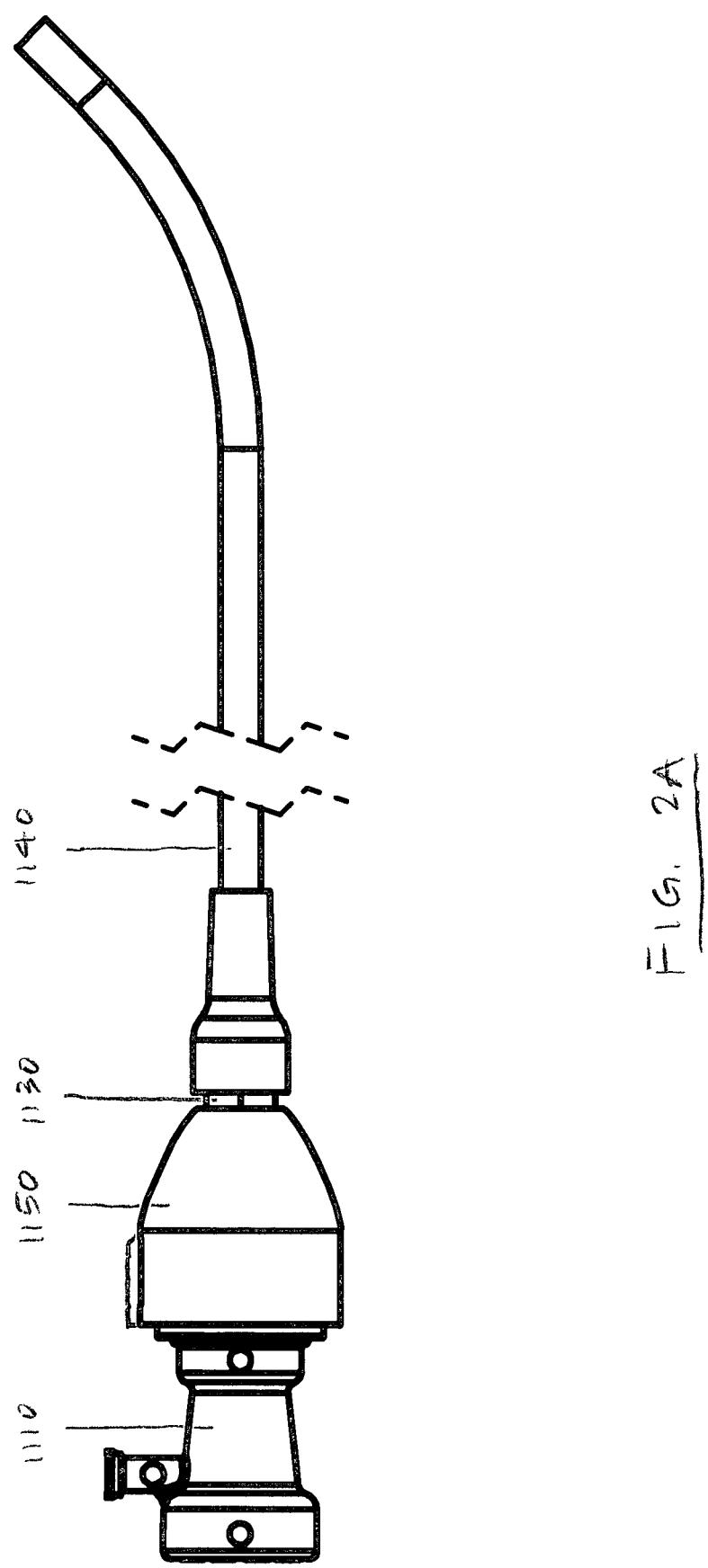

INTRODUCER SHEATHS

BACKGROUND

Introducer sheaths are used to access a vessel to allow a catheter or other device to be inserted into the vessel. An introducer sheath may include a sheath hub with a side port and side tube. The side port and side tube allow an agent to be delivered through the introducer sheath. The side port and side tube also allow a fluid to be aspirated from the introducer sheath.

The introducer sheath may be used with a dilator and advanced over a guidewire that has been inserted into the vessel. The introducer sheath may be rotated to facilitate advancement through the skin and into the vessel.

The introducer sheath may have a curved tip to facilitate access to a desired part of the anatomy. The introducer sheath may be rotated to point the curved tip in a desired direction.

Rotating the introducer sheath may wrap the side tube around the sheath hub and other parts of the introducer sheath. The side tube may need to be manually unwound from the sheath hub and other parts of the introducer sheath. The side tube may also become kinked and restrict flow through the side tube.

What is needed is an introducer sheath that can be rotated without tangling a side tube around the sheath hub and other parts of the introducer sheath.

SUMMARY

Introducer sheaths are described. In one embodiment, an introducer sheath comprises a sheath hub, a fixed housing coupled to the sheath hub, a rotating element rotatably coupled to the fixed housing, a sheath tube fixedly coupled to the rotating element, and a lock coupled to the rotating element. The lock is capable of preventing the rotating element and the sheath tube from rotating with respect to the sheath hub.

Methods of using an introducer sheath are described. In one embodiment, a method comprises rotating a sheath tube with respect to a sheath hub, and locking the sheath tube to prevent the sheath tube from rotating with respect to the sheath hub. The sheath tube is rotatably coupled to the sheath hub.

BRIEF DESCRIPTION OF THE DRAWINGS

FIGS. 1A-1G show one embodiment of an introducer sheath 1100. FIGS. 1A-1B show side views of introducer sheath 1100. FIG. 1C shows a perspective view of introducer sheath 1100. FIG. 1D shows an exploded perspective view of introducer sheath 1100. FIG. 1E shows an exploded cross-sectional view of introducer sheath 1100. FIG. 1F shows a cross-sectional view of introducer sheath 1100 in an unlocked position. FIG. 1G shows a cross-sectional view of introducer sheath 1100 in a locked position.

FIGS. 2A-2D show one embodiment of a method for using introducer sheath 1100. FIG. 2A shows lock 1150 locked. FIG. 2B shows unlocking lock 1150. FIG. 2C shows rotating sheath tube 1140 with respect to sheath hub 1110. FIG. 2D shows locking lock 1150.

DESCRIPTION

Introducer sheaths are described having a sheath tube that may be rotated independently with respect to a sheath hub. This prevents a side tube from becoming wrapped around the sheath hub and/or other parts of the introducer sheath. In addition, the sheath tube may be locked in place and prevented from rotating with respect to the sheath hub. This prevents the sheath tube from inadvertently rotating while in use.

Figure 1A:
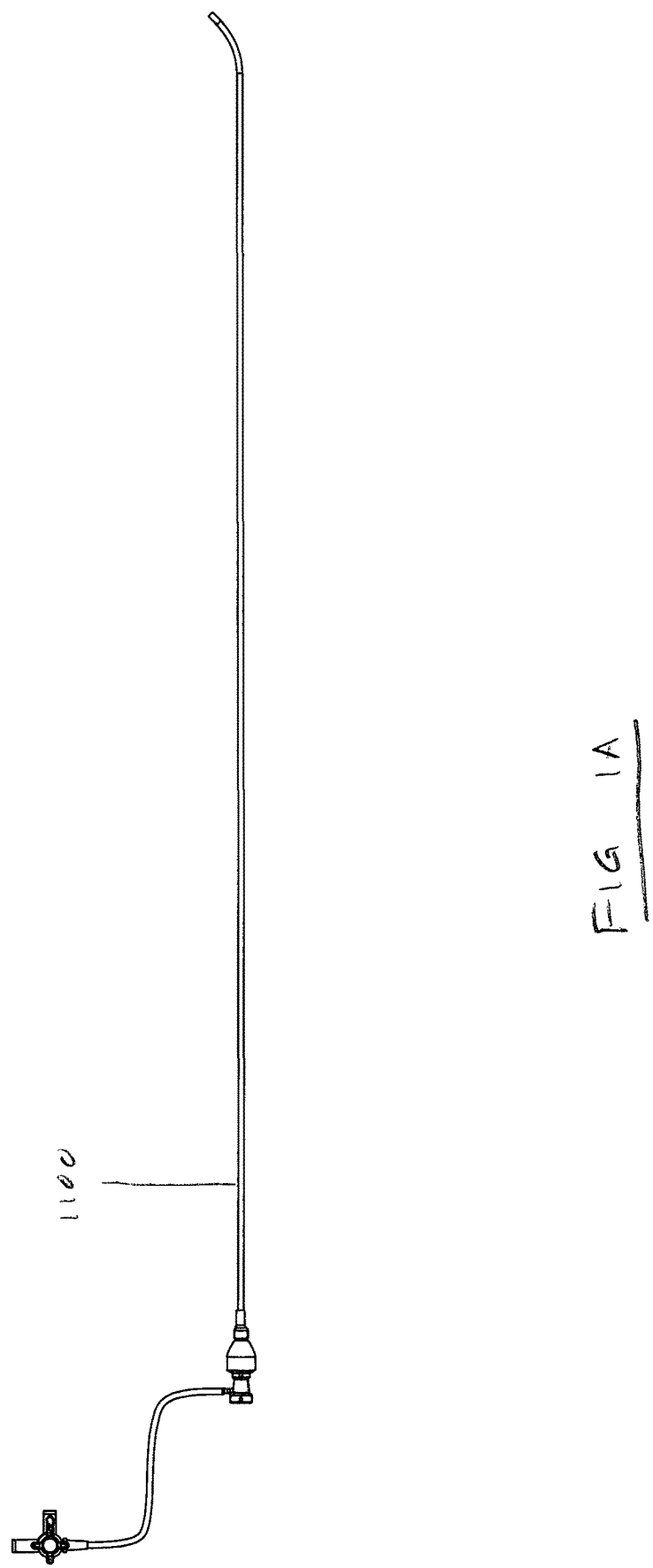
Figure 1B:
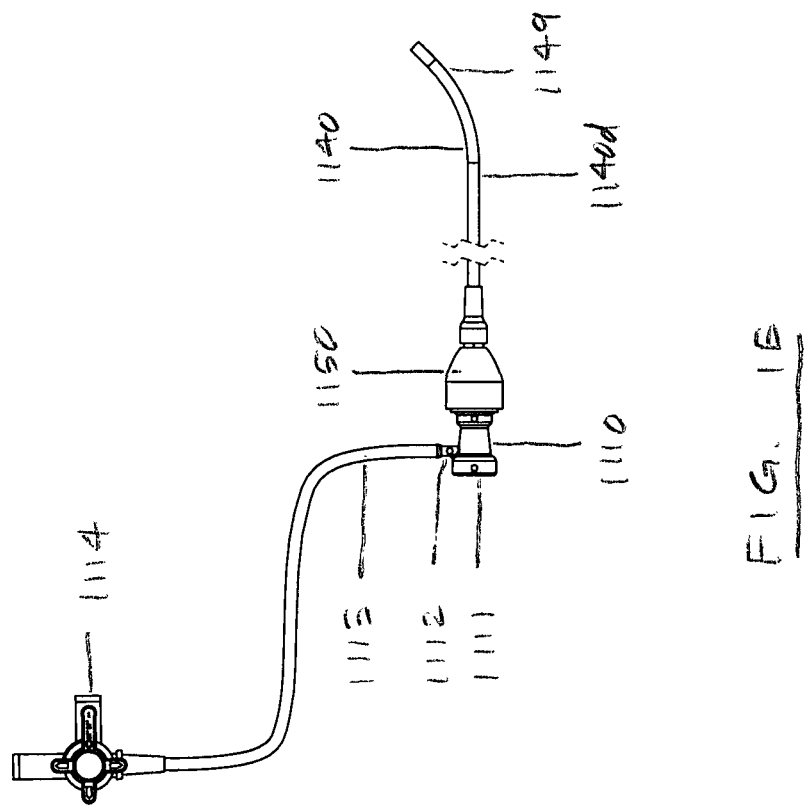
Figure 1D:
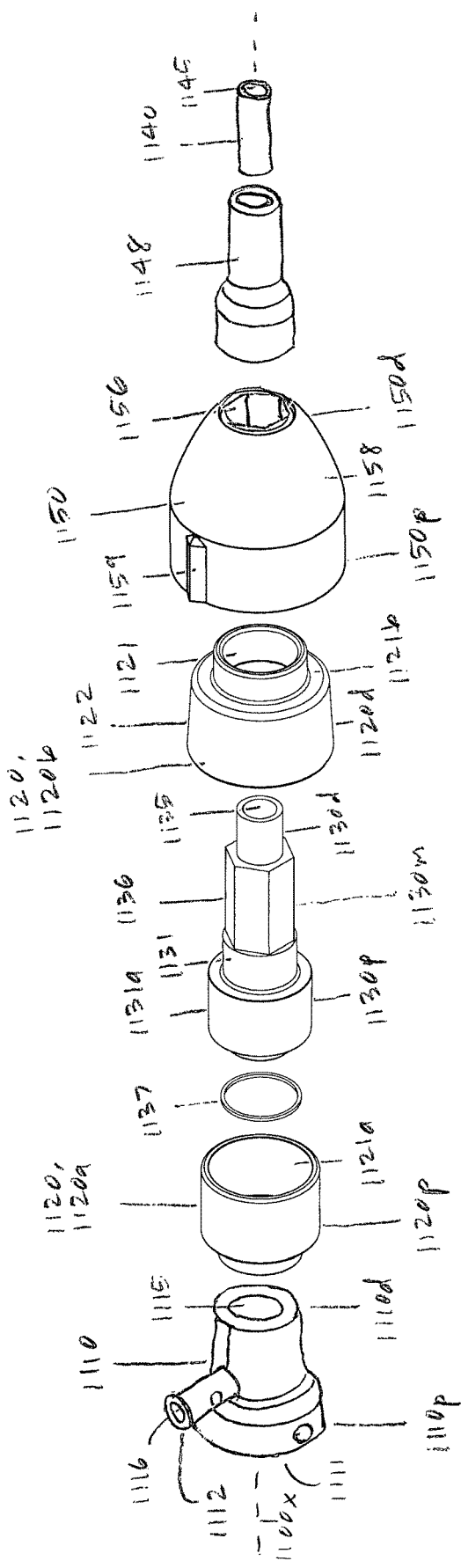
Figure 1E:
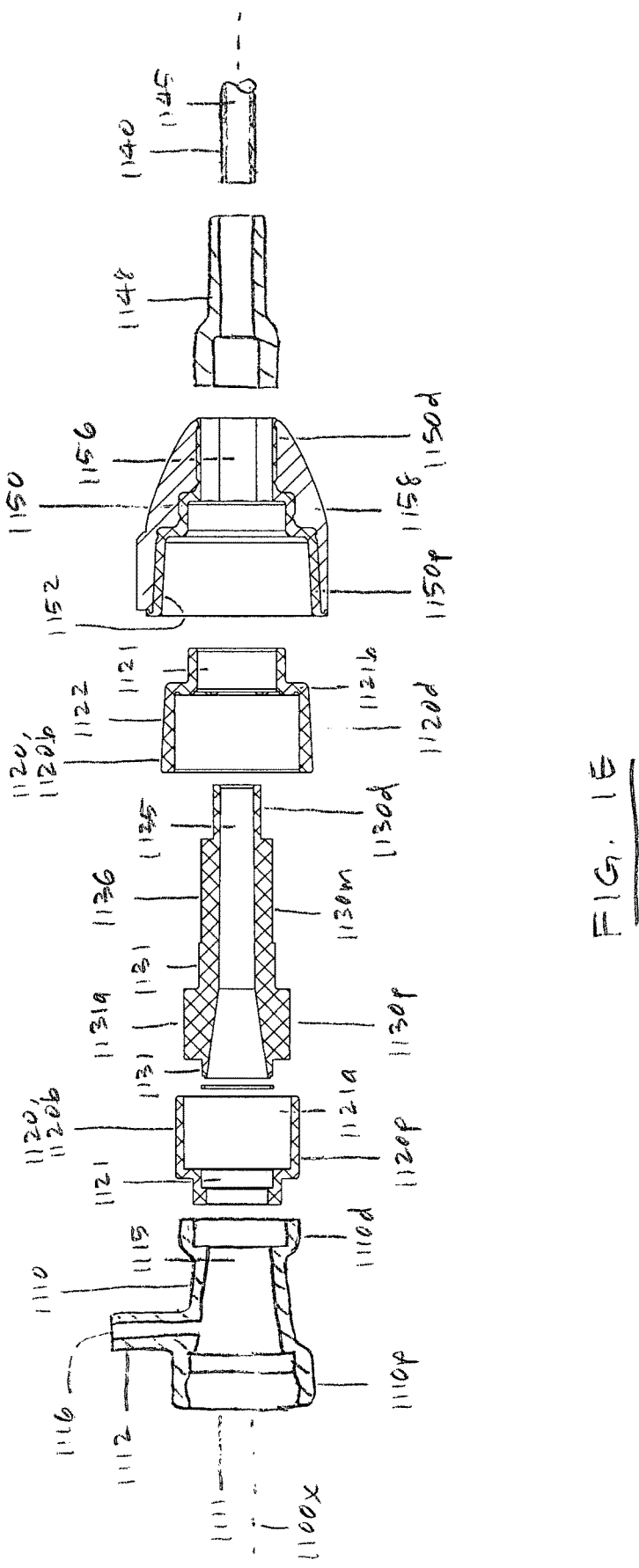
Figure 16:
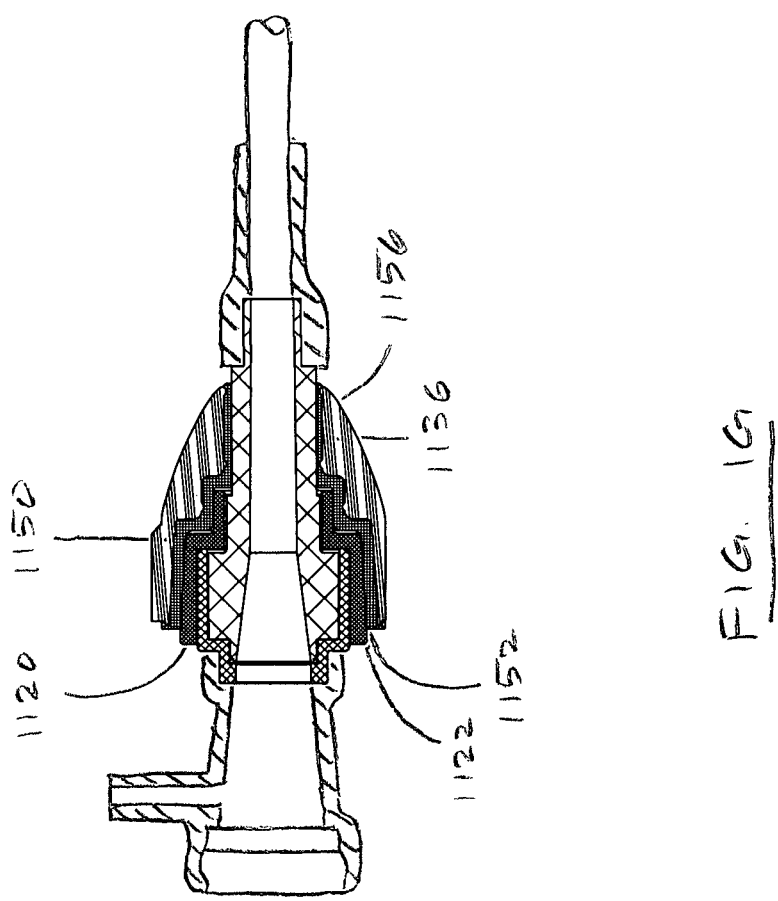
Figure 28:
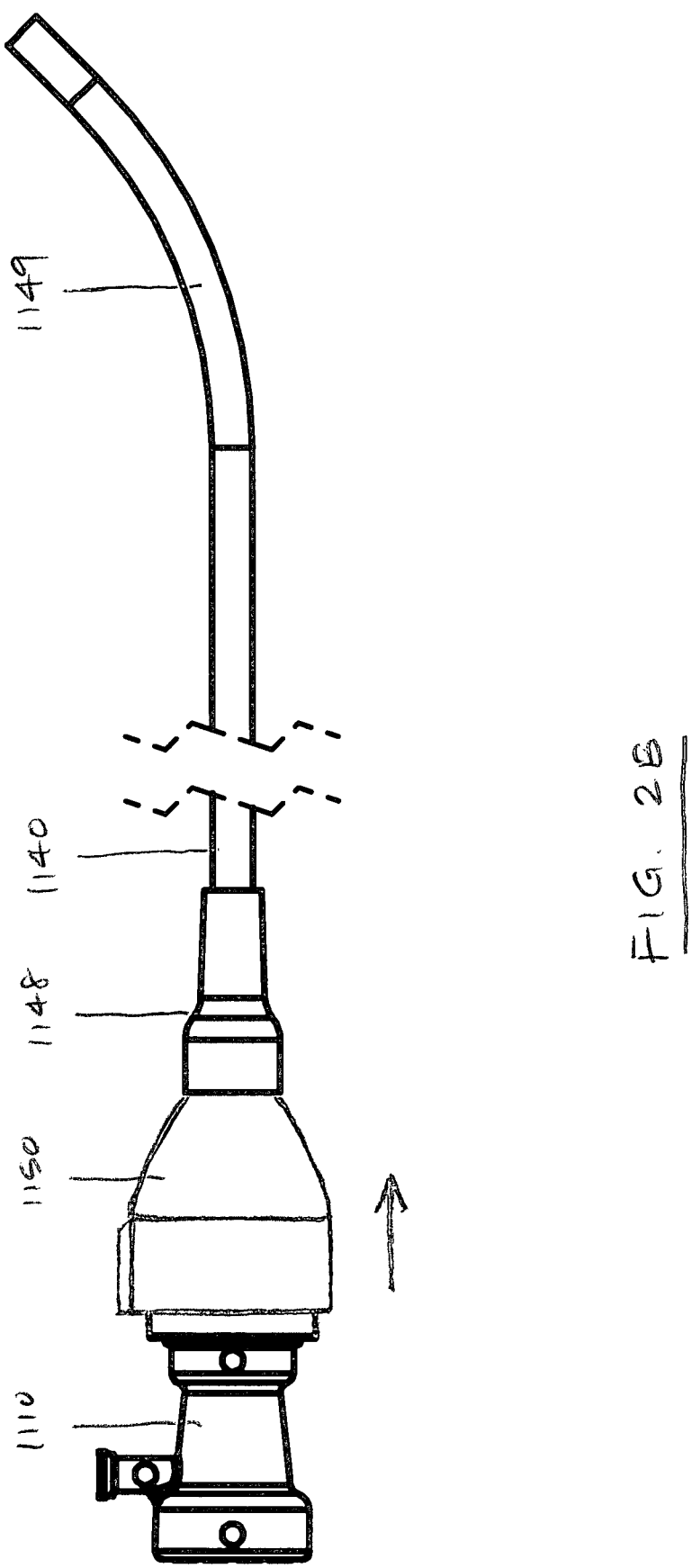

FIGS. 1A-1F show one embodiment of an introducer sheath 1100. FIGS. 1A-1B show side views of introducer sheath 1100. FIG. 1C shows a perspective view of introducer sheath 1100. FIG. 1D shows an exploded perspective view of introducer sheath 1100. FIG. 1E shows an exploded cross-sectional view of introducer sheath 1100. FIG. 1F shows a cross-sectional view of introducer sheath 1100 in an unlocked position. FIG. 1G shows a cross-sectional view of introducer sheath 1100 in a locked position.

Introducer sheath 1100 may include a sheath hub 1110. Sheath hub 1110 may include a proximal portion 1110$p$ and a distal portion 1110$d$. Introducer sheath 1100 may have a longitudinal axis 1100$x$.

Sheath hub 1110 may include a main port 1111 and a main lumen 1115. Main port 1111 may provide access to main lumen 1115. Sheath hub 1110 may include a side port 1112 and a side lumen 1116. Side port 1112 may provide access to side lumen 1116. Side port 1112 may be coupled to a side tube 1113 and a stopcock 1114. Side lumen 1116 may be in fluid communication with main lumen 1115. Side lumen 1116 may be connected at an angle to main lumen 1115, such as at 90 degrees.

Introducer sheath 1100 may include a fixed housing 1120, a rotating element 1130, and a sheath tube 1140. Introducer sheath 1100 may include a lock 1150.

Fixed housing 1120 may include a proximal portion 1120$p$ and a distal portion 1120$d$. Fixed housing 1120 may be fixedly coupled to sheath hub 1110. Proximal portion 1120$p$ of fixed housing 1120 may be coupled to distal portion 1110$d$ of sheath hub 1110. Fixed housing 1120 may include one or more housing pieces. For example, fixed housing 1120 may include a first housing piece 1120$a$ coupled to a second housing piece 1120$b$ to form fixed housing 1120. Fixed housing 1120 may be formed separately from sheath hub 1110. Alternatively, one or more pieces of fixed housing 1120 may be formed as a single piece with sheath hub 1110.

Rotating element 1130 may include a proximal portion 1130$p$, a middle portion 1130$m$, and a distal portion 1130$d$. Rotating element 1130 is rotatably coupled to fixed housing 1120 and thus sheath hub 1110. Rotating element 1130 may include a lumen 1135. Lumen 1135 may have a width that is uniform or varying. Lumen 1135 of rotating element 1130 may be in fluid communication with main lumen 1115 of sheath hub 1110.

Sheath tube 1140 may include a proximal portion 1140$p$ and a distal portion 1140$d$. Sheath tube 1140 may be coupled to rotating element 1130. Proximal portion 1140$p$ of sheath tube 1140 may be coupled to distal portion 1130$d$ of rotating element 1130. Alternatively, sheath tube 1140 may be formed as a single piece with rotating element 1130. Sheath tube 1140 may include a lumen 1145. Lumen 1145 of sheath tube 1140 may be in fluid communication with lumen 1135 of rotating element 1130. Sheath tube 1140 may include a curved tip 1149 at distal portion 1140$d$.

Lock 1150 may include a proximal portion 1150$p$ and a distal portion 1150$d$. Lock 1150 may be coupled to rotating element 1130.

Fixed housing 1120 may include a bore 1121. Bore 1121 may be substantially cylindrical. Bore 1121 may include a collar track 1121$a$. Collar track 1121$a$ may be a section of bore 1121 having a larger diameter than a remainder of bore 1121. Collar track 1121*a* may form a shoulder 1121*b* distal to collar track 1121*a*.

Rotating element 1130 may include a core 1131. Core 1131 may be at proximal portion 1130*p* of rotating element 1130. Core 1131 may be substantially cylindrical. Core 1131 may have diameters of varying dimensions. Core 1131 may include a collar 1131*a*. Collar 1131*a* may be a section of core 1131 having a larger diameter than a remainder of core 1131. Alternatively, collar 1131*a* may be formed separately from core 1131 and coupled to core 1131.

Bore 1121 is configured to receive core 1131. Core 1131 is configured to rotate inside bore 1121. Collar track 1121*a* is configured to receive collar 1131*a*. Collar 1131*a* is configured to rotate inside collar track 1121*a*. Bore 1121 may support core 1131 both proximally and distally of collar 1131*a*. Alternatively, bore 1121 may support core 1131 only distally of collar 1131*a*.

Core 1131 may be configured to rotate freely inside bore 1121. Core 1131 may have a smaller diameter than bore 1121. Collar 1131*a* may have a smaller diameter than collar track 1121*a*, but a larger diameter than a remainder of bore 1121. Shoulder 1121*b* may prevent collar 1131*a* and thus rotating element 1130 from moving distally.

A seal 1137 may be coupled to proximal portion 1130*p* of rotating element 1130. Seal 1137 may be placed between proximal portion 1130*p* of rotating element 1130 and bore 1121. Alternatively, seal 1137 may be placed between proximal portion 1130*p* of rotating element 1130 and main lumen 1115 of sheath hub 1110. Shoulder 1121*b* may urge proximal portion 1130*p* of rotating element 1130 against seal 1137.

Rotating element 1130 may include a slide segment 1136. Slide segment 1136 may be at middle portion 1130*m* of rotating element 1130. Slide segment 1136 may be formed on an outside surface of rotating element 1130. Slide segment 1136 may have a transverse cross section that is non-circular. Slide segment 1136 may have a cross section that is hexagonal. Alternatively, slide segment 1136 may have a cross section that is oval, polygonal, star- or gear-shaped, or other suitable shape.

Lock 1150 may include a slide bore 1156. Slide bore 1156 may be at distal portion 1150*d* of lock 1150. Slide bore 1156 may be formed on an inside surface of lock 1150. Slide bore 1156 may have a cross section that is configured to engage slide segment 1136. Slide bore 1156 may have a cross section that is similar to that of slide segment 1136. Slide bore 1156 may have a transverse cross section that is non-circular. Slide bore 1156 may have a cross section that is hexagonal. Alternatively, slide bore 1156 may have a cross section that is oval, polygonal, star- or gear-shaped, or other suitable shape.

Slide bore 1156 is configured to receive slide segment 1136. Slide bore 1156 and slide segment 1136 may be configured so that lock 1150 rotates together with rotating element 1130. Slide bore 1156 and slide segment 1136 may have transverse cross sections that are non-circular, which prevent slide segment 1136 from rotating with respect to slide bore 1156 and lock 1150. Slide bore 1156 may have a larger width than slide segment 1136, but not a width so large as to allow slide segment 1136 to rotate independently inside slide bore 1156.

Lock 1150 may be configured to slide along slide segment 1136 through slide bore 1156. Slide segment 1136 may have a longer length than slide bore 1156. Lock 1150 may slide proximally and distally along slide segment 1136.

Lock 1150 may be configured to slide freely along slide segment 1136. Slide bore 1156 may have a larger width than slide segment 1136. Alternatively, lock 1150 may be configured to not slide freely along slide segment 1136. Slide bore 1156 may have a width that forms a slight interference fit with slide segment 1156.

Fixed housing 1120 may include a first locking surface 1122, shown in FIGS. 1D-1G. First locking surface 1122 may be formed on an outside surface of fixed housing 1120. First locking surface 1122 may have a transverse cross section that is substantially circular. First locking surface 1122 may be tapered, having a larger width towards proximal portion 1120*p* of fixed housing 1120 and a smaller width towards distal portion 1120*d* of fixed housing 1120. First locking surface 1122 may be shaped like a frustum. Alternatively, first locking surface 1122 may have a width that is substantially uniform.

Lock 1150 may include a second locking surface 1152 shown in FIGS. 1E-1G. Second locking surface 1152 may be at proximal portion 1150*p* of lock 1150. Second locking surface 1152 may be formed on an inside surface of lock 1150. Second locking surface 1152 may have a shape that is configured to engage first locking surface 1122 of fixed housing 1120. Second locking surface 1152 may have a transverse cross section that is substantially circular. Second locking surface 1152 may be shaped like a frustum. Second locking surface 1152 may be tapered, having a larger width towards proximal portion 1150*p* of lock 1150 and a smaller width towards distal portion 1150*d* of lock 1150. Alternatively, second locking surface 1152 may have a width that is substantially uniform.

Lock 1150 has an unlocked position configured to allow rotating element 1130 and sheath tube 1140 to rotate with respect to sheath hub 1110, shown in FIG. 1F. Lock 1150 may be moved into the unlocked position by sliding lock 1150 in a distal direction until second locking surface 1152 of lock 1150 is not in contact with first locking surface 1122 of fixed housing 1120.

Lock 1150 has a locked position configured to prevent rotating element 1130 and sheath tube 1140 from rotating with respect to sheath hub 1110, shown in FIG. 1G. Lock 1150 may be moved into the locked position by sliding lock 1150 in a proximal direction until second locking surface 1152 of lock 1150 comes into contact with first locking surface 1122 of fixed housing 1120 and forms an interference fit with first locking surface 1122 of fixed housing 1120. Lock 1150 and thus rotating element 1130 and sheath tube 1140 are prevented from rotating with respect to fixed housing 1120 and sheath hub 1110.

When first locking surface 1122 and second locking surface 1152 have transverse cross sections that are substantially circular, rotating element 1130 may have an angular position that is infinitely adjustable. When first locking surface 1122 and/or second locking surface 1152 are tapered, the the interference fit between first locking surface 1122 and second locking surface 1152 tightens as lock 1150 is moved proximally.

A grip 1158 may be coupled to lock 1150. Grip 1158 may be coupled around lock 1150. Grip 1158 may be textured to make it easier to manipulate lock 1150.

A marker 1159 may be coupled to lock 1150 and/or rotating element 1130. Marker 1159 may be aligned with curved tip 1149. Marker 1159 may indicate a direction in which curved tip 1149 is curved or pointed.

Sheath tube 1140 may be fixedly coupled to rotating element 1130 with a sleeve 1148. Sheath tube 1140 and rotating element 1130 rotate together. Sleeve 1148 may be coupled around proximal portion 1140*p* of sheath tube 1140 and distal portion 1130*d* of rotating element 1130. Distal portion 1130d of rotating element 1130 may have a smaller width than slide segment 1136. Sleeve 1148 may have a portion that has a larger width than slide bore 1156, and acts as a distal stop for lock 1150.

Introducer sheath 1100 allows sheath tube 1140 to rotate independently with respect to sheath hub 1110. This allows sheath tube 1140 to be rotated and the position of curved tip 1149 to be changed without having to rotate sheath hub 1110 and side port 1112. This prevents side tube 1113 from wrapping around sheath hub 1110 and/or other parts of introducer sheath 1100.

Introducer sheath 1100 allows sheath tube 1140 to be locked in place, and prevents sheath tube 1140 from rotating with respect to sheath hub 1110. This prevents sheath tube 1140 from inadvertently rotating while in use, and prevents the position of curved tip 1149 from inadvertently moving while in use.

For a sheath hub 1110 without a side port 1112 and/or a sheath tube 1140 without a curved tip 1149, it may still be useful to have a sheath tube 1140 that can be rotated independently of the sheath hub 1110 and locked in place.

FIGS. 2A-2D show one embodiment of a method for using introducer sheath 1100.

FIG. 2A shows lock 1150 locked. Lock 1150 has been moved in a proximal direction into the locked position. Lock 1150 prevents rotating element 1130 and sheath tube 1140 from rotating with respect to sheath hub 1110.

FIG. 2B shows unlocking lock 1150. Lock 1150 is moved in a distal direction into the unlocked position. Lock 1150 may be stopped from traveling further distally by sleeve 1148.

Figure 2C:
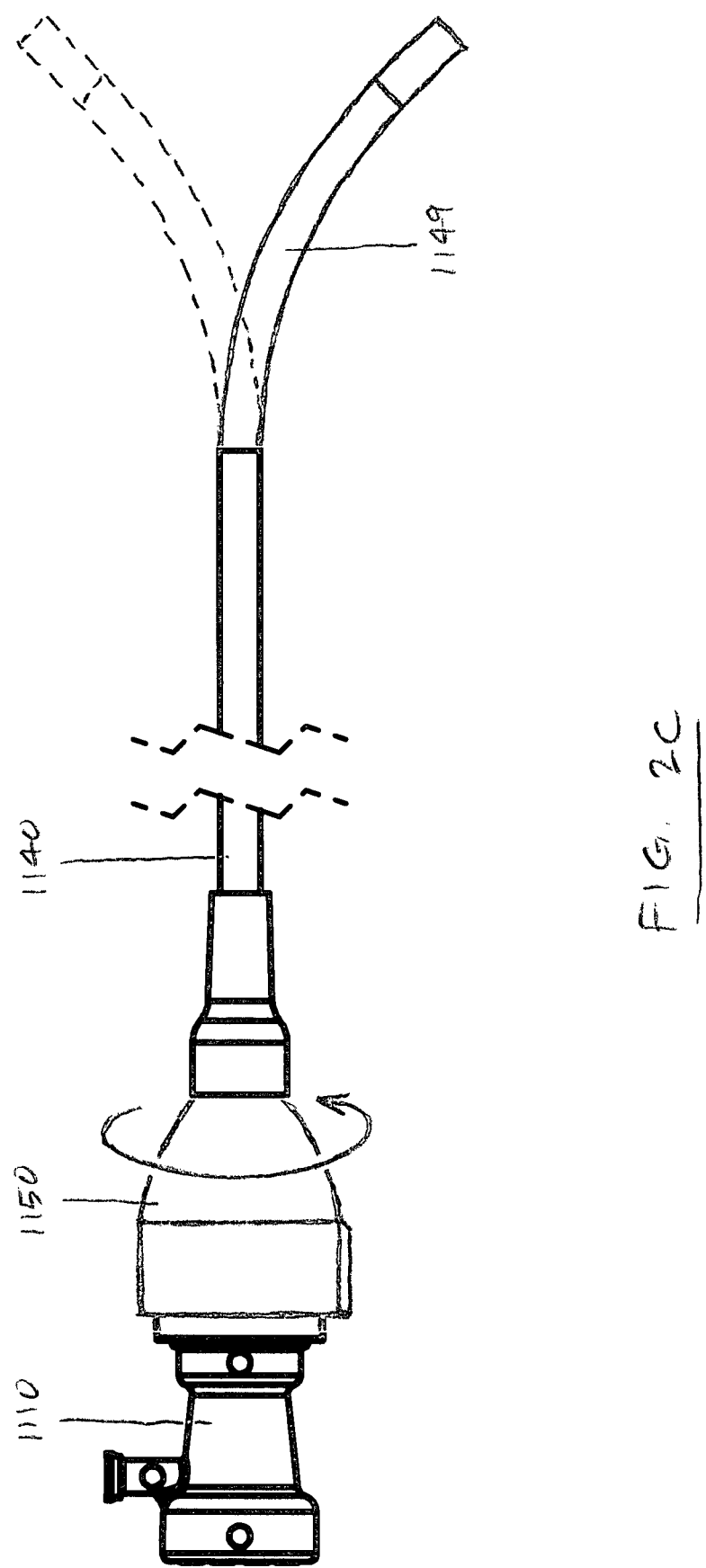

FIG. 2C shows rotating sheath tube 1140 with respect to sheath hub 1110. Lock 1150, rotating element 1130, and sheath tube 1140 rotate together. Sheath tube 1140 may be rotated by rotating lock 1150. Sheath tube 150 may also be rotated by rotating sheath tube 1140 and/or sleeve 1148 directly. Sheath tube 1140 may be rotated to point curved tip 1149 in a desired direction. Marker 1159 may be used to show the direction of curved tip 1149 if curved tip 1149 is hidden from view.

Figure 2D:
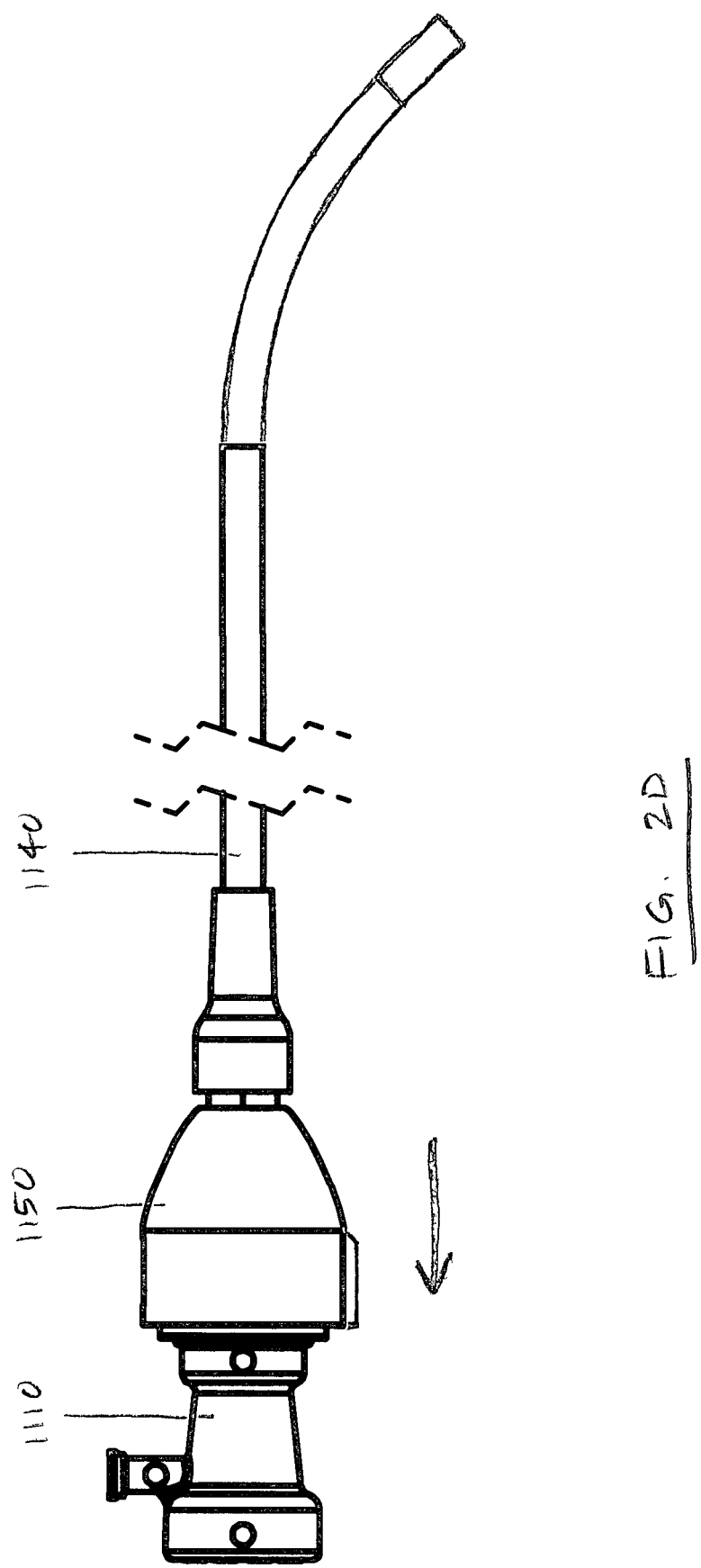

FIG. 2D shows locking lock 1150. Lock 1150 is moved in a proximal direction into the locked position. Lock 1150 prevents rotating element 1130 and sheath tube 1140 from rotating with respect to sheath hub 1110.

While the foregoing has been with reference to particular embodiments of the invention, it will be appreciated by those skilled in the art that changes in these embodiments may be made without departing from the principles and spirit of the invention.

What is claimed is:

1. An introducer sheath, comprising:
a sheath hub;
a fixed housing coupled to the sheath hub, the fixed housing including a first locking surface formed on an outside surface of the fixed housing;
a rotating element rotatably coupled to the fixed housing;
a sheath tube fixedly coupled to the rotating element and rotatably coupled to the sheath hub; and
a lock coupled to the rotating element, the lock capable of engaging the first locking surface to selectively prevent the rotating element and the sheath tube from rotating with respect to the sheath hub and the fixed housing.

2. The introducer sheath of claim 1, wherein the sheath hub includes a side port.

3. The introducer sheath of claim 1, wherein the sheath tube includes a curved tip.

4. The introducer sheath of claim 3, further comprising a marker coupled to the lock, the marker aligned with the curved tip.

5. The introducer sheath of claim 1, wherein a proximal portion of the fixed housing is fixedly coupled to a distal portion of the sheath hub.

6. The introducer sheath of claim 1, wherein a proximal portion of the sheath tube is coupled to a distal portion of the rotating element.

7. The introducer sheath of claim 1, wherein a lumen of the rotating element is in fluid communication with a main lumen of the sheath hub.

8. The introducer sheath of claim 1, wherein a lumen of the sheath tube is in fluid communication with a lumen of the rotating element.

9. The introducer sheath of claim 1, wherein the rotating element includes a slide segment, and the lock includes a slide bore.

10. The introducer sheath of claim 9, wherein the slide segment and the slide bore have transverse cross sections that are non-circular.

11. The introducer sheath of claim 9, wherein the slide segment and the slide bore have cross sections that are hexagonal.

12. The introducer sheath of claim 9, wherein the slide segment is configured to slidably engage with the slide bore.

13. The introducer sheath of claim 9, wherein the lock is configured to slide along the slide segment through the slide bore.

14. The introducer sheath of claim 1, wherein the lock includes a second locking surface.

15. The introducer sheath of claim 14, wherein the first locking surface and the second locking surface are tapered.

16. The introducer sheath of claim 14, wherein the lock has an unlocked position configured to allow the rotating element and the sheath tube to rotate, and the lock has a locked position configured to prevent the rotating element and the sheath tube from rotating.

17. The introducer sheath of claim 16, wherein the first locking surface is configured not to contact the second locking surface when the lock is in the unlocked position.

18. The introducer sheath of claim 16, wherein the first locking surface is configured to form an interference fit with the second locking surface when the lock is in the locked position.

19. A method of using an introducer sheath, the method comprising:
providing an introducer sheath as in claim 1;
using the rotating element to rotate the sheath tube with respect to the sheath hub; and
using the lock to selectively prevent the sheath tube from rotating with respect to the sheath hub.

20. An introducer sheath, comprising:
a sheath hub;
a fixed housing coupled to the sheath hub, the fixed housing including a locking surface formed on an outside surface of the fixed housing;
a rotating element rotatably coupled to the fixed housing;
a sheath tube fixed coupled to the rotating element and rotatably coupled to the sheath hub; and
a locking means coupled to the rotating element, the locking means capable of cooperating with the locking surface to selectively prevent the rotating element and the sheath tube from rotating with respect to the sheath hub and the fixed housing.

* * * * *